United States Patent [19]

Connor et al.

[11] 4,012,422
[45] Mar. 15, 1977

[54] PROCESS FOR THE CYCLIZATION OF ARYL (METHYLSULFINYL)-METHYL KETONES AND NOVEL COMPOUNDS PRODUCED THEREBY

[76] Inventors: David T. Connor, 15 Westminster Drive, Parsippany, N.J. 07054; Maximilian Von Strandtmann, 47 Erie Ave., Rockaway, N.J. 07866

[22] Filed: Apr. 25, 1975

[21] Appl. No.: 571,890

Related U.S. Application Data

[62] Division of Ser. No. 464,706, April 26, 1974, Pat. No. 3,920,699.

[52] U.S. Cl. .......................................... 260/345.2
[51] Int. Cl.² ...................................... C07D 311/02
[58] Field of Search ................................ 260/345.2

[56] References Cited
UNITED STATES PATENTS

| | | | |
|---|---|---|---|
| 3,699,128 | 10/1972 | Strandtmann et al. | 260/345.2 |
| 3,699,129 | 10/1972 | Strandtmann et al. | 260/345.2 |
| 3,798,240 | 3/1974 | Strandtmann et al. | 260/345.2 |
| 3,801,644 | 4/1974 | Strandtmann et al. | 260/592 |
| 3,850,966 | 11/1974 | Cohen et al. | 260/345.2 |

OTHER PUBLICATIONS

Becker et al., J. Amer. Chem. Soc., 85, 3410 (1963).
Corby et al., J. Amer. Chem. Soc., 84, 866 (1962).

*Primary Examiner*—James O. Thomas, Jr.
*Assistant Examiner*—Nicky Chan

[57] ABSTRACT

The invention relates to novel compounds having the formulas I and III:

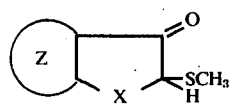 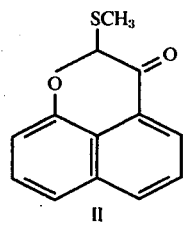

I  II wherein, in formula I, X is -O- or -N-COR wherein R is lower alkyl or aryl, and Z is

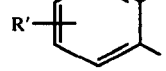 or 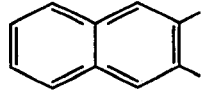

wherein R' is hydrogen, halogen or alkoxy. The compounds of this invention are prepared by a novel process which involves the cyclization of the corresponding aryl(methylsulfinyl)methyl ketones. The compounds of this invention having formulas I and III are useful in the treatment of hyperacidity and for alleviating allergic manifestations.

1 Claim, No Drawings

PROCESS FOR THE CYCLIZATION OF ARYL (METHYLSULFINYL)-METHYL KETONES AND NOVEL COMPOUNDS PRODUCED THEREBY

This is a division of application Ser. No. 464,706 filed Apr. 26, 1976, now U.S. Pat. No. 3,920,699.

DESCRIPTION OF THE INVENTION

The present invention relates to novel substituted-2-(methylthio)-3(2H)-benzofuranones and novel substituted-2-(methylthio)-3-indolinones having the formula I:

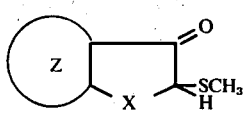

wherein X is —O— or —N—COR wherein R is lower alkyl or aryl, and Z is

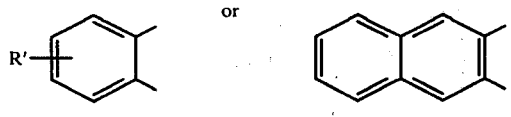

wherein R' is hydrogen, halogen or alkoxy; and to novel 2-(methylthio)naphtho[1,8-bc]pyran-3-(2H)-one having the formula III:

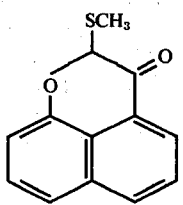

This invention also includes within its scope a novel process for preparing the above compounds as well as certain novel intermediates used in their preparation.

The novel compounds of the invention having formula I, as defined above, are prepared by cyclizing the corresponding aryl-(methylsulfinyl)methyl ketone having the formula II:

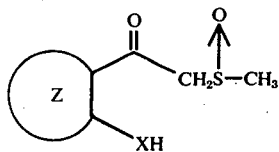

wherein X is —O— or —N—COR wherein R is lower alkyl or aryl, and Z is

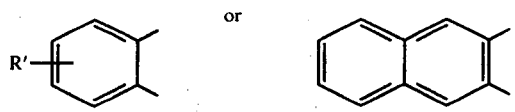

wherein R' is hydrogen, halogen or alkoxy.

This cyclization reaction involves refluxing the keto sulfoxide starting material II with an equivalent of trifluoroacetic acid in a suitable solvent, such as benzene, toluene or the like, for 1 to 2 hours.

The starting materials having the formula II as described above wherein X is oxygen are prepared as described in U.S. Pat. No. 3,801,644, patented Apr. 2, 1974: dimethyl sulfoxide is reacted with sodium hydride in an inert solvent to which is added an appropriately substituted ortho-hydroxy aromatic ester; the temperature is maintained at not more than 50° C and the reaction product is precipitated by the addition of a nonpolar solvent. Substituted o-hydroxy-ω-(methylsulfinyl)acetophenones or substituted o-hydroxy-ω-(methylsulfinyl)acetonaphthones used as starting materials for certain of the compounds of this invention are obtained by this method. For example, 2'-hydroxy-2-(methylsulfinyl)-acetophenone; 2'-hydroxy-3'-methoxy-2-(methylsulfinyl)acetophenone; 5'-chloro-2'-hydroxy-2-(methylsulfinyl)acetophenone; 3'-hydroxy-2-(methylsulfinyl)-2'-acetonaphthone may be prepared by this method.

Starting materials having the formula II wherein X is —N—COR, with R representing lower alkyl or aryl, are prepared as described in M. von Strandtmann et al., Journal Organic Chemistry, 36: 1742–1744 (1971) by the addition of sodium methylsulfinylmethide to the appropriately 3-substituted-2,4-benzoxazin-1-one, to obtain such compounds as 2'[(methylsulfinyl)acetyl]-benzanilide; 2'[(methylsulfinyl)acetyl]naphthylbenzamide; 2'[(methylsulfinyl)acetyl]-loweralkyl-benzamide, and the like.

Similarly, novel compounds of the invention having the formula III:

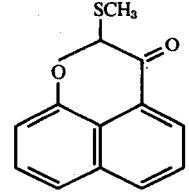

are prepared by refluxing a compound of the formula IV:

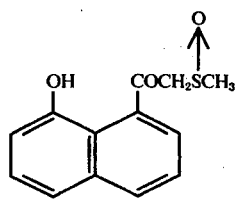

dissolved in a suitable solvent, with an equivalent of trifluoroacetic acid for 1 to 2 hours. Starting material IV, (8'hydroxy-2-(methylsulfinyl)-1'acetonaphthone) is also novel and is prepared by the addition of sodium methylsulfinylmethide to 2H-naphtho[1,8-bc]furan-2-one.

Among the preferred compounds of the invention having formula I there may be mentioned those wherein R represents 1 to 3 carbon lower alkyl or phenyl; and R' is hydrogen, chloro or 1 to 3 carbon lower alkoxy.

In all of the structures in the specification and in the claims the term "alkyl" and the alkyl portion of "alkoxy" is meant to include straight and branched chain alkyl radicals containing from 1 to 7 carbon atoms, for example, methyl, ethyl, propyl, isopropyl, butyl, n-hexyl and the like. The term "halogen" encompasses fluorine, bromine, chlorine and iodine. The term "aryl" denotes unsaturated cyclic hydrocarbon radicals derived from benzene, such as phenyl or naphthyl.

The compounds of this invention are active orally or when injected, for the prevention of allergic and asthmatic reactions in mammals such as cats, dogs, rats, guinea pigs and the like, at dosage levels of 25 to 150 mg/kg of body weight. Thus, 7-methoxy-2-(methylthio)-3(2H)-benzofuranone shows a 34% inhibition of the allergic response at 25 mg/kg when tested in the passive cutaneous anaphalaxis (PCA) screen, which is a modification of procedures described by I. Mota, *Life Sciences*, 7, 465 (1963) and Z. Ovary and O. Bier, *Proc. Soc. Exptl. Biol. Med.*, 81, 585 (1952). Consequently, the compounds I and III of this invention are useful in the treatment of asthma, hay fever and other allergic conditions.

In addition to the above-mentioned utility, the compounds of this invention having formulas I and III also inhibit hyperacidity in aforementioned mammals when administered orally or by injection at dosages of 10 to 100 mg/kg of body weight. For example, when 2-(methylthio)-3(2H)-benzofuranone is tested according to the procedure described by H. Shay, et al., *Gastroenterology*, 5, 43 (1945), in the pylorus ligated rat, at a dose of 20 mg/kg of body weight, injected intraperitoneally, it caused a reduction of 49.6% in volume of gastric acid and a 28% reduction in the ion acid compared to controls. Thus, compounds having the formulas I and III are useful in the treatment of gastric ulcers.

In order to use the compounds of the invention having formulas I and III as described above, they may be formulated with standard pharmaceutical carriers such as lactose, mannitol, dicalcium phosphate and the like, into dosage forms such as tablets, capsules and the like. They can also be combined with parenterally acceptable vehicles such as polyethylene glycol, sesame oil, peanut oil or the like, for injectable dosage forms.

To further illustrate the practice of this invention the following examples are included.

EXAMPLE I

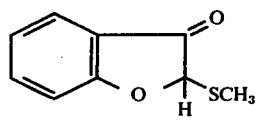

2-(Methylthio)-3(2H)-benzofuranone.

2-Hydroxy-1-[(methylsulfinyl) acetyl]benzene (1.5 g 0.0075m) and trifluoroacetic acid (1.5 g) are refluxed in benzene (25 ml) for one hour under nitrogen. The solvent is removed under reduced pressure to give a pale yellow oil which crystallizes on standing. Recrystallization from ethanol gave white crystals, (0.611 g 45%), m.p. 81°–82° C.

Anal. Calcd. for $C_9H_8O_2S$: C, 59.98; H, 4.47; S, 17.79. Found: C, 60.12; H, 4.49; S, 17.78.

EXAMPLE II

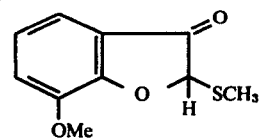

7-Methoxy-2-(methylthio)-3(2H)-benzofuranone.

Prepared by the general method described in Example I, starting with 2-hydroxy-3-methoxy-1-[(methylsulfinyl)acetyl]benzene. Recrystallization from absolute ethanol gives white crystals, (89 g 65%), m.p. 103°–105° C.

Anal. Calcd. for $C_{10}H_{10}O_3S$: C, 57.13; H, 4.79; S, 15.25. Found: C, 57.28; H, 4.97; S, 15.36.

EXAMPLE III

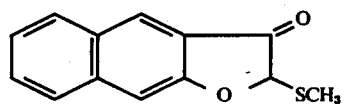

2-(Methylthio)-naphtho[2,3-b]furan-3(2H)-one.

Prepared by the general procedure described in Example I, starting with 3-hydroxy-2-[(methylsulfinyl)acetyl]naphthalene. Recrystallization from ethanol gives yellow crystals, (1.5 g 81%), m.p. 118°–120° C.

Anal. Calcd. for $C_{13}H_{10}SO_2$: C, 67.80; H, 4.38; S, 13.92. Found: C, 67.64; H, 4.46; S, 13.94.

EXAMPLE IV

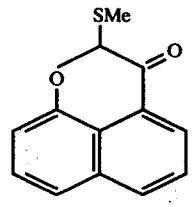

2-(Methylthio)naphtho[1,8-bc]pyran-3(2H)-one.

Prepared by the general procedure described in Example I, starting with 8-hydroxy-1-[(methylsulfinyl)acetyl]naphthalene (1 g). Recrystallization from ethanol gives yellow-brown crystals, (600 mg 64%), m.p. 89°–91° C.

Anal. Calcd. for $C_{13}H_{10}O_2S$: C, 67.80; H, 4.38; S, 13.92. Found: C, 67.60; H, 4.49; S, 13.89.

EXAMPLE V

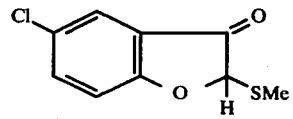

5-Chloro-2-(methylthio)-3(2H)-benzofuranone.

5-Chloro-2-hydroxy-1-[(methylsulfinyl)acetyl]benzene (6.0 g) and trifluoroacetic acid (6 g) are refluxed in benzene (50 ml) for one hour under nitrogen. The solvent is removed under reduced pressure to give a yellow oil, which crystallizes on standing. Recrystallization from ethanol gives white crystals. (3.0 g 54%) m.p. 76°–78° C.

Anal. Calcd. for $C_9H_7ClO_2S$: C, 50.36; H, 3.29; Cl, 16.51; S, 14.94. Found: C, 50.18; H, 3.22; Cl, 16.73; S, 14.70.

EXAMPLE VI

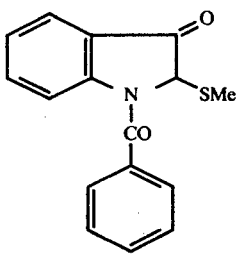

1-Benzoyl-2-(methylthio)-3-indolinone.

2'-[(methylsulfinyl)-acetyl]benzanilide (7 g) is refluxed in benzene containing 1 equivalent of trifluoroacetic acid for 1 hour. The solvents are removed under reduced pressure to give an oil which crystallizes on standing. Recrystallization from ethyl acetate gives 1-benzoyl-2-(methylthio)-3-indolinone (4.5 g 67%) m.p. 126°–128° C.

Anal. Calcd. for $C_{16}H_{13}NO_2S$: C, 67.82; H, 4.62; N, 4.94; S, 11.32. Found: C, 67.66; H, 4.70; N, 4.94; S, 11.29.

We claim:

1. A process for preparing a compound of the formula III:

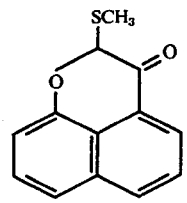

which comprises reacting a compound of the formula IV:

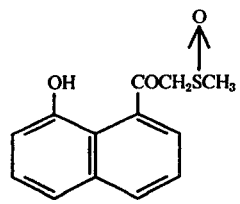

with an equivalent amount of trifluoroacetic acid, in an inert solvent, at reflux temperature.

* * * * *